United States Patent
Matsumoto et al.

(10) Patent No.: US 10,064,789 B2
(45) Date of Patent: Sep. 4, 2018

(54) POLYMERIZABLE COMPOSITION AND KIT FOR POLYMERIZABLE COMPOSITION

(71) Applicant: GC Corporation, Bunkyo-ku (JP)

(72) Inventors: Naofumi Matsumoto, Itabashi-ku (JP); So Ishizuka, Itabashi-ku (JP); Mika Wako, Itabashi-ku (JP)

(73) Assignee: GC Corporation, Bunkyo-ku (JP)

( * ) Notice: Subject to any disclaimer, the term of this patent is extended or adjusted under 35 U.S.C. 154(b) by 97 days.

(21) Appl. No.: 14/916,134

(22) PCT Filed: Sep. 11, 2014

(86) PCT No.: PCT/JP2014/074103
§ 371 (c)(1),
(2) Date: Mar. 2, 2016

(87) PCT Pub. No.: WO2015/037670
PCT Pub. Date: Mar. 19, 2015

(65) Prior Publication Data
US 2016/0213577 A1   Jul. 28, 2016

(30) Foreign Application Priority Data
Sep. 13, 2013 (JP) ................................. 2013-190281

(51) Int. Cl.
| | | |
|---|---|---|
| *A61K 6/083* | (2006.01) | |
| *C08L 33/10* | (2006.01) | |
| *A61K 6/00* | (2006.01) | |
| *C08F 2/44* | (2006.01) | |
| *C08F 4/40* | (2006.01) | |
| *A61K 6/02* | (2006.01) | |

(52) U.S. Cl.
CPC .............. *A61K 6/083* (2013.01); *A61K 6/005* (2013.01); *A61K 6/0017* (2013.01); *A61K 6/0023* (2013.01); *A61K 6/0047* (2013.01); *A61K 6/024* (2013.01)

(58) Field of Classification Search
None
See application file for complete search history.

(56) References Cited

U.S. PATENT DOCUMENTS

| | | | |
|---|---|---|---|
| 3,541,068 A | | 11/1970 | Taylor |
| 5,250,641 A | | 10/1993 | Kumagai et al. |
| 5,290,172 A | * | 3/1994 | Sakuma ............... A61K 6/0023 106/35 |
| 5,609,675 A | * | 3/1997 | Noritake ............... C04B 14/062 106/35 |
| 5,925,690 A | * | 7/1999 | Fuchigami ........... A61K 6/0088 523/118 |
| 6,852,775 B1 | | 2/2005 | Soglowek et al. |
| 2004/0068041 A1 | * | 4/2004 | Nakayama ................. C08J 3/24 524/493 |
| 2005/0009946 A1 | * | 1/2005 | Oguri .................... A61K 6/0023 522/184 |
| 2006/0252846 A1 | * | 11/2006 | Yoshiyama .......... A61K 6/0029 523/118 |
| 2008/0248086 A1 | * | 10/2008 | Asgari .................. A61L 27/446 424/426 |
| 2009/0048366 A1 | | 2/2009 | Torii et al. |
| 2011/0053116 A1 | | 3/2011 | Hecht et al. |

FOREIGN PATENT DOCUMENTS

| | | | | |
|---|---|---|---|---|
| EP | 1 634 562 A1 | 3/2006 | | |
| EP | 1634562 A1 | * 3/2006 | ........... A61K 6/0073 | |
| JP | 61-126007 A | 6/1986 | | |
| JP | 62-175410 A | 8/1987 | | |
| JP | 62-175412 A | 8/1987 | | |
| JP | 05-178714 A | 7/1993 | | |
| JP | 2003-502351 A | 1/2003 | | |
| JP | 2003-105008 A | 4/2003 | | |
| JP | 2005-289961 A | 10/2005 | | |
| WO | 2007/88628 A1 | 8/2007 | | |

OTHER PUBLICATIONS

International Search Report dated Nov. 18, 2014 for PCT/JP2014/074103 filed on Sep. 11, 2014.

* cited by examiner

*Primary Examiner* — Peter A Salamon
(74) *Attorney, Agent, or Firm* — Oblon, McClelland, Maier & Neustadt, L.L.P.

(57) ABSTRACT

A polymerizable composition includes at least one of an acrylate compound and a methacrylate compound; a barbiturate compound; an amino carboxylic acid-based chelating agent; a peroxy compound; and filler.

13 Claims, No Drawings

POLYMERIZABLE COMPOSITION AND KIT FOR POLYMERIZABLE COMPOSITION

BACKGROUND OF THE INVENTION

1. Field of the Invention

An aspect of the present invention is related to at least one of a polymerizable composition and a kit for a polymerizable composition.

2. Description of the Related Art

A polymerizable composition for dental use includes filler, a (meth) acrylate compound, and a polymerization initiator for polymerizing the (meth) acrylate compound as main ingredients. Various material characteristics are exhibited by the polymerized (meth) acrylate compound. For the polymerizable composition, a composition composed of forms of powder and liquid and using a polymerization initiator of a peroxide and a tertiary amine has been used from a long time ago (See, for example, U.S. Pat. No. 3,541,068). However, with a form composed of powder and liquid, there is a problem that an operation in dental treatment becomes complicated.

In a case where, in order to eliminate this complicatedness, the polymerizable composition is prepared in a paste form by incorporating a polymerization initiator into (meth) acrylate compound, there is a problem that the polymerization initiator causes (meth) acrylate compound to polymerize with time, thereby the composition forms a gel, and the polymerizable composition has inferior storage stability. Therefore, this polymerization initiator cannot be used for a packaging mode in a paste form, but is limited for a use of a product in a powder form. In addition, there has been a method for curing a resin for dental use using a barbiturate compound (pyrimidinetrione derivative), which has a higher ability to generate radicals than the above-described polymerization initiator and has a high polyerization performance though it is a form of liquid and powder in the same way as above, as the polymerization initiator (See, for example, Japanese Unexamined Patent Application Publication No. H5-178714).

Instead of the polymerizable composition, as above, which is composed of powder and liquid, and usage of which is limited, a composition of a type in which two kinds of paste are mixed is developed (See, for example, Japanese Unexamined Patent Application Publication No. 2003-105008). This polymerization composition is a polymerizable composition in a paste form characterized by comprising a first paste composed of (meth) acrylate having at least one unsaturated double bond, filler and a pyrimidinetrione compound; a second paste composed of (meth) acrylate having at least one unsaturated double bond, filler, an organic halogen compound and an organic metal compound or a third paste composed of (meth) acrylate having at least one unsaturated double bond, filler and an organic halogen compound; and a fourth paste composed of (meth) acrylate having at least one unsaturated double bond, filler and an organic metal compound.

However, this polymerizable composition in a paste form has insufficient reactivity because an organic peroxide (peroxy compound) is not combined with the pyrimidinetrione compound (barbiturate compound).

A polymerizable composition divided into two pastes, i.e. a paste combining the organic peroxide with the barbiturate compound and a paste including a metallic ion and a chloride, may be considered. However, there is a problem that in a case where the organic peroxide is combined with the barbiturate compound, reactivity becomes too great and the paste may gelatinize during storage. In a case of incorporating a great amount of polymerization inhibitor in order to avoid the gelatinization, there is a problem that the polymerization and curing reaction may come insufficient this time. In order to exhibit various intended material characteristics in a material for dental use, a (meth) acrylate compound is required to be polymerized sufficiently upon being used.

To remedy the problem that the polymerizable composition, in which an organic peroxide and a barbiturate compound are included in the same paste, may gelatinize, it is known that including a plasticizer, which does not polymerize, of about 1% to 30% in the composition is effective (See, for example, Japanese Translation of PCT International Application Publication No. JP-T-2003-502351). However, it is pointed out that because the plasticizer does not polymerize finally, in a case of placing in an oral cavity for a long time, the plasticizer may be eluted and may adversely affect the patient. Moreover, there is a problem that it may be covered with plasticizer a surface of which does not cure immediately after polymerization, and the plasticizer may adhere to a hand of an operator, thereby an operational feeling becomes worse. Furthermore, there is a problem that in a case where the polymerizable composition is an adhesive, the adhesion force may be adversely affected.

SUMMARY OF THE INVENTION

According to one embodiment of the present invention, a polymerizable composition including at least one of an acrylate compound and a methacrylate compound; a barbiturate compound; an amino carboxylic acid-based chelating agent; a peroxy compound; and a filler is provided.

According to another embodiment of the present invention, a kit for a polymerizable composition including a first polymerizable composition and a second polymerizable composition, wherein the first polymerizable composition includes at least one of a first acrylate compound and a first methacrylate compound, a barbiturate compound, an amino carboxylic acid-based chelating agent, a peroxy compound, and a first filler, and wherein the second polymerizable composition includes at least one of a second acrylate compound and a second methacrylate compound, an organic halogen compound, an organic metallic compound, and a second filler, is provided.

DESCRIPTION OF THE PREFERRED EMBODIMENTS

One paste of a polymerizable composition in two pastes form according to an embodiment of the present invention will be referred to as a first paste. The first paste includes (b) a barbiturate compound, (c) an amino carboxylic acid-based chelating agent, (d) a peroxy compound and (e) filler in (a) (meth) acrylate compound. Moreover, other necessary additive agent as a polymerizable composition is included, but a plasticizer is not included.

The (meth) acrylate compound of a component (a) used in an embodiment of the present invention refers to various kinds of monomers, oligomers and prepolymers of acrylate or methacrylate compound. More specifically, the (meth) acrylate compound used in the present invention could be methyl (meth) acrylate, ethyl (meth) acrylate, isopropyl (meth) acrylate, n-butyl (meth) acrylate, isobutyl (meth) acrylate, hydroxypropyl (meth) acrylate, tetrahydrofurfuryl (meth) acrylate, glycidyl (meth) acrylate, 2-hydroxyethyl (meth) acrylate, 2-hydroxypropyl (meth) acrylate, 3-hydroxypropyl (meth) acrylate, 2-methoxyethyl (meth) acrylate, 2-ethoxyethyl (meth) acrylate, 2-ethylhexyl (meth) acrylate, benzyl (meth) acrylate, 2-hydroxy-1,3-di (meth) acryloxy propane, ethylene glycol di (meth) acrylate, diethylene glycol di (meth) acrylate, triethylene glycol di (meth) acrylate, butylene glycol di (meth) acrylate, neopentyl glycol di (meth) acrylate, 1,3-butanediol di (meth) acrylate, 1,4-butanediol di (meth) acrylate, 1,6-hexanediol di (meth) acrylate, trimethylolpropane tri (meth) acrylate, trimethylolethane tri (meth) acrylate, pentaerythritol tri (meth) acrylate, trimethylolmethane tri (meth) acrylate, pentaerythritol tetra (meth) acrylate, polybutylene glycol di (meth) acrylate, or bisphenol A diglycidyl (meth) acrylate. Monomers, oligomers, and prepolymers of these compounds can be suitably used. Moreover, as for (meth) acrylates having a urethane bond, di-2-(meth) acryloxyethyl-2,2,4-trimethylhexamethylene dicarbamate, 1,3,5-tris[1,3-bis{(meth)acryloyloxy}-2-propoxycarbonylaminohexane]-1,3,5-(1H,3H, 5H) triazine-2,4,6-trione, 2,2-bis-[4-{3-(meth)acryloyloxy-2-hydroxypropyl}-phenyl] propane, 2,2-bis[4-{(meth) acryloxyethoxy]phenyl] propane, and the like can be used. In addition, the (meth) acrylate having urethane bond could be (meth) acrylate of urethane oligomer including 2,2'-di (4-hydroxycyclohexyl) propane, 2-oxypanone, hexamethylene diisocyanate, and 2-hydroxyethyl (meth) acrylate, and (meth) acrylate of urethane oligomer including 1,3-butanediol, hexamethylene diisocyanate, and 2-hydroxyethyl (meth) acrylate. These (meth) acrylates and acrylates can be used alone or by mixing two or more kinds.

In the present embodiment, as for (meth) acrylate compound of the component (a), (meth) acrylate having an acid group can be used. A (meth) acrylate compound having an acid group imparts an adhesive property to the polymerizable composition to adhere to a tooth, dental restorative materials, which are ceramics such as zirconia or alumina, and an alloy including noble metals. The (meth) acrylate compound having an acid group is preferably a (meth) acrylate compound having a phosphate group or a carboxyl group. Thus, a (meth) acrylate having one or plural phosphate groups or carboxyl groups in one molecule can be used. Because the phosphate group has acidity stronger than the carboxyl group, the phosphate group has higher effect for dissolving a smear layer of a tooth surface and for tooth demineralization. Particularly, the phosphate group can significantly improve adhesion to enamel. A (meth) acrylate having a phosphate group could be 2-(meth) acryloyloxyethyldihydrogen phosphate, bis[2-(meth) acryloyloxyethyl] hydrogen phosphate, 2-(meth) acryloyloxyethylphenylhydrogen phosphate, 6-(meth) acryloyloxyhexyldihydrogen phosphate, 6-(meth) acryloyloxyhexylphenylhydrogen phosphate, 10-(meth) acryloyloxydecyldihydrogen phosphate, 1,3-di(meth) acryloylpropane-2-dihydrogen phosphate, 1,3-di(meth) acryloylpropane-2-phenylhydrogen phosphate, bis[5-{2-(meth) acryloyloxyethoxycarbonyl}heptyl]hydrogen phosphate, or the like. Particularly, 10-(meth) acryloyloxydecyldihydrogen phosphate is preferable because of having an excellent adhesive property and stability of the (meth) acrylate compound itself. The (meth) acrylate compound having the phosphate group can be used alone or by mixing two or more kinds.

A (meth) acrylate compound having the carboxyl group could be 4-(meth) acryloxyethyltrimellitic acid, 4-(meth) acryloxyethyltrimellitic acid anhydride, 4-(meth) acryloxydecyltrimellitic acid, 4-(meth) acryloxydecyltrimellitic acid anhydride, 11-(meth) acryloyloxy-1,1-undecanedicarboxylic acid, 1,4-di(meth) acryloyloxypyromellitic acid, 2-(meth) acryloyloxyethylmaleic acid, 2-(meth) acryloyloxyethylphthalic acid, 2-(meth) acryloyloxyethylhexahydrophthalic acid, or the like. Particularly, 4-(meth) acryloxyethyltrimellitic acid and 4-(meth) acryloxyethyltrimellitic acid anhydride are preferable in that these have an excellent adhesive property.

The (meth) acrylate compound of the component (a) used in the present embodiment is incorporated so as to be a base material of the composition. The (meth) acrylate compound is preferably incorporated in an amount of 50 to 95 wt % in the first paste, and an amount of 45 to 90 wt % in the second paste.

The polymerizable composition in two pastes form according to an embodiment of the present invention does not include a plasticizer which may be eluted in an oral cavity, despite its excellent storage stability while using a peroxy compound. A plasticizer which is not included in the polymerizable composition according to the present embodiment could be phthalate ester plasticizer, adipate ester plasticizer, trimellitic acid ester plasticizer, polyester plasticizer, phosphate ester plasticizer and citrate ester plasticizer.

As the phthalate ester plasticizer, dioctyl phthalate, di-isononyl phthalate, di-isodecyl phthalate, dibutyl phthalate or the like is exemplified. As the adipate ester plasticizer, dioctyl adipate or di-isononyl adipate is exemplified. Moreover, as the trimellitic acid ester plasticizer, trimellitic acid trioctyl is exemplified. As the polyester plasticizer, low-molecular polyester is exemplified. As the phosphate ester plasticizer, tricresyl phosphate is exemplified. Suitable citrate ester plasticizers may include, for example, acetyl tributyl citrate.

The barbiturate compound of the component (b) used in the present embodiment is incorporated into the first paste as an initiator of redox polymerization. The amount of incorporation is preferably 0.1 to 2 wt % in the first paste. In a case where it is less than 0.4 wt %, it is difficult to obtain an effect as the redox polymerization initiator. In a case of incorporating in an amount greater than 2 wt %, the barbiturate compound becomes insoluble in the first paste and the polymerization may be incomplete. It is preferably 0.1 to 1 wt. As the barbiturate compound, for example, the following compound can be used, i.e. 1,3,5-trimethyl barbiturate, 1,3,5-triethyl barbiturate, 1,3-dimethyl-5-ethyl barbiturate, 1,5-dimethyl barbiturate, 1-methyl-5-ethyl barbiturate, 1-methyl-5-propyl barbiturate, 5-ethyl barbiturate, 5-propyl barbiturate, 5-butyl barbiturate, 1-benzyl-5-phenyl barbiturate, 1-cyclohexyl-5-ethyl barbiturate. These compounds can be used alone or by mixing two or more kinds.

The amino carboxylic acid-based chelating agent of the component (c) used in the present embodiment is incorporated into the first paste in order to eliminate metallic ions mixed during manufacturing process or from a raw material. An amount of incorporation is preferably 0.00001 to 2 wt %. In a case where it is less than 0.00001 wt %, it is difficult to obtain a sufficient effect. In a case of incorporating in an amount greater than 2 wt %, the effect is almost unchanged.

The amino carboxylic acid-based chelating agent of the component (c) could be ethylenediamine-N,N,N',N'-tetraacetic acid (EDTA), diethylene triamine-N,N,N',N'',N''-pentaacetic acid (DTPA), N-hydroxyethyl ethylenediamine-N,N',N'-triacetic acid (HEDTA), nitrilotriacetic acid (NTA), O,O'-bis (2-aminoethyl) ethylene glycol-N,N,N',N'-tetraacetic acid (EGTA), trans-1,2-diaminocyclohexane-N,N, N',N'-tetraacetic acid (CyDTA), and a salt thereof.

The amino carboxylic acid-based chelating agent of the component (c) may be directly incorporated into the (meth)

acrylate compound of the component (a), but may be dissolved in water of the component (i) before incorporating into the first paste.

The water of the component (i) is preferably incorporated in an amount of 0.05 to 5 wt % in the first paste. If it is less than 0.05 wt %, it may be difficult to incorporate into the first paste sufficiently if the amino carboxylic acid-based chelating agent of the component (c) is ethylene diamine tetraacetic acid or a salt thereof. In a case where it is greater than 5 wt %, it may adversely affect strength of the composition after polymerization.

Use of the peroxy compound of the component (d) used in the present embodiment helps generate radicals and promotes the polymerization reaction in conjunction with the barbiturate derivative. The amount of incorporation is preferably 0.05 to 2 wt % in the first paste. In a case where it is less than 0.05 wt %, it is difficult to obtain a sufficient polymerization reaction. In a case of incorporating in an amount greater than 2 wt %, the storage stability tends to decrease.

As the peroxy compound, carboxylic acid peroxy ester or hydroperoxide is exemplified. As a polyfunctional carboxylic acid peroxy ester, carbonate peroxy ester is also included. An adequate compound could be, for example, carbonate-diisopropyl-peroxy diester, neodecanoate-tertiary butyl-peroxy ester, neodecanoate-tertiary amyl-peroxy ester, maleate-tertiary butyl-mono peroxy ester, benzoate-tertiary butyl-peroxy ester, 2-ethyl hexanoate-tertiary butyl-peroxy ester, 2-ethyl hexanoate-tertiary amyl-peroxy ester, carbonate-mono isopropyl ester-mono tertiary butyl-peroxy ester, carbonate-dicyclohexyl-peroxy ester, carbonate-dimyristyl-peroxy ester, carbonate-dicetyl-peroxy ester, carbonate-di (2-ethyl hexyl)-peroxy ester, carbonate-tertiary butyl-peroxy-(2-ethyl hexyl) ester or 3,5,5-trimethyl hexanoate-tertiary butyl-peroxy ester, benzoate-tertiary amyl-peroxy ester, acetate-tertiary butyl-peroxy ester, carbonate-di (4-tertiary butyl-cyclohexyl)-peroxy ester, neodecanoate-cumene-peroxy ester, pivalate-tertiary amyl-peroxy ester and pivalate-tertiary butyl-peroxy ester, cumene hydroperoxide, 1,1,3,3-tetramethyl butyl hydroperoxide, diisopropyl benzene hydroperoxide, tertiary butyl hydroperoxide, para-menthane hydroperoxide.

Another paste of the polymerizable composition in two pastes formed in accordance with the embodiment of the present invention will be referred to as a second paste. The second paste includes (g) an organic halogen compound, (h) an organic metallic compound, and (e) filler in (a) the above-described (meth) acrylate compound. Moreover, another necessary additive agent as a polymerizable composition is included, but a plasticizer is not included, in the same way as the first paste.

For the (meth) acrylate compound used for the second paste, the same compound as that used for the first paste may be used.

A radical polymerization initiator used for the second paste is a reducing material for the redox polymerization, i.e. (g) the organic halogen compound and (h) the organic metallic compound.

The organic halogen compound of the component (g) may be, specifically, benzyl tributyl ammonium chloride, benzyl dimethyl cetyl ammonium chloride, benzyl dimethyl stearyl ammonium chloride, benzyl triethyl ammonium bromide, benzyl trimethyl ammonium chloride, cetalkonium chloride, cetyl pyridinium bromide, cetyl pyrimidinium chloride, cetyl triethyl ammonium bromide, didecyl dimethyl ammonium chloride, dilauryl dimethyl ammonium chloride, benzyl lauryl dimethyl ammonium chloride, domiphen bromide, lauryl trimethyl ammonium chloride, tetra-N-butyl ammonium bromide, tetra-N-butyl ammonium chloride, tetra-N-butyl ammonium iodide, tetradecyl trimethyl ammonium bromide, tetraethyl ammonium bromide, tetraethyl ammonium iodide, trioctyl methyl ammonium chloride, or the like. These organic halogen compounds can be used alone or by mixing two or more kinds.

The organic halogen compound of the component (g) is preferably incorporated in the second paste in an amount of 0.001 to 2 wt %, more preferably 0.01 to 1 wt %, and especially more preferably 0.05 to 0.5 wt %. In a case where it is less than 0.001 wt %, it is difficult to obtain an effect as a reducing agent. In a case where it is greater than 2 wt %, it is unnecessary for the second paste, and it is difficult to obtain a polymerization reaction.

The organic metallic compound of the component (h) could be, specifically, acetyl acetone copper, 4-cyclohexyl butyrate copper, gluconate copper, acetate copper, oleate copper, acetyl acetone manganese, naphthenate manganese, octylate manganese, acetyl acetone cobalt, naphthenate cobalt, acetyl acetone lithium, acetate lithium, acetyl acetone zinc, naphthenate zinc, acetyl acetone nickel, acetate nickel, acetyl acetone aluminum, acetyl acetone calcium, acetyl acetone chromium, acetyl acetone iron, naphthenate sodium, rare earth octoate or the like. These organic metallic compounds can be used alone or by mixing two or more kinds.

The organic metallic compound of the component (h) is preferably incorporated in the second paste in an amount of 0.001 to 0.2 wt %, more preferably 0.01 to 0.1 wt %. In a case where it is less than 0.001 wt %, it is difficult to obtain an effect as a reducing agent. In a case where it is greater than 0.2 wt %, a composition tends to get discolored after polymerization.

The polymerizable composition in two pastes form according to the embodiment of the present invention incorporates (e) filler in both the first paste and the second paste. Filler incorporated conventionally in the polymerizable composition for dental use can be used without restriction especially.

The filler of the component (e) could be, glasses, such as anhydrous silicic acid, barium glass, alumina glass, potassium glass, fluoroaluminosilicate glass, powder of synthetic zeolite, phosphate calcium, feldspar, fumed silica, silicate aluminum, silicate calcium, carbonate magnesium, hydrous silicic acid, hydrous calcium silicate, hydrous aluminum silicate, or quartz. Moreover, a glass including an oxide of barium, strontium, yttrium or the like, or a sulfide or a fluoride thereof is used as necessary according to its X-ray imaging property.

These fillers may be subjected to a surface treatment with a silane coupling agent, such as γ-methacryloxypropyl trimethoxy silane, vinyltrichlorosilane, vinyltriethoxysilane, vinyltrimethoxysilane, vinyltriacetoxysilane, or vinyltri (methoxyethoxy) silane. It goes without saying that acetic acid or the like may be added to the above-described silane coupling agent. Especially, anhydrous silicic acid, hydrous silicic acid, hydrous calcium silicate, hydrous aluminum silicate are preferable since they have an effect of preventing the polymerizable composition in a paste form before polymerization from gelating even when stored for long periods.

An organic-inorganic mixed filler may be used, which is prepared by mixing in advance the filler of the component (e) with a (meth) acrylate compound, curing the filler, and thereafter pulverizing the cured filler. These fillers can be used alone or by mixing two or more kinds.

Meanwhile, of course, fillers of different materials may be used for respective pastes of the first paste and the second paste.

Moreover, fine silicic acid of 0.01 to 0.1 μm with 0 to 20 wt % may be used in order to adjust viscosity of each paste.

It is a matter of course that the polymerizable composition of two pastes formed in accordance with the embodiment of the present invention includes a polymerizable composition including two or more pastes by further separating the components of the first paste and/or the second paste into a plurality of pastes, as long as the above-described action principle for enhancing polymerization reaction and storage stability is satisfied.

As the other additive agent, an antioxidizing agent, ultraviolet absorbing agent, a pigment or the like can be suitably used.

EXAMPLES

Polymerizable compositions in two pastes form are prepared with the ratios shown in TABLE 1A, 1B and 1C and TABLE 2. The following test is conducted for the compositions of respective examples and of a comparative example and evaluation is performed.

<Confirmation Test for Storage Stability>

The first paste of 0.25 g and the second paste of 0.2 g are malaxated for 10 seconds. A metallic mold having diameter of 6.5 mm and height of 5 mm is filled with the malaxated paste. Variation in temperature of the malaxated paste is measured by a T-shaped thermocouple.

A time point at which a heat generation by polymerization is the highest is referred to as a curing time from a start of the malaxation. Moreover, a temperature thereof is referred to as a heat generation peak temperature.

The curing time and the heat generation peak temperature are confirmed respectively in a case of storing for six weeks at 60° C. Results are summarized in TABLE 1A, TABLE 1B, and TABLE 1C, and TABLE 2.

Abbreviations in the tables are as follows:
Component (a)
UDMA: di-2-methacryloxy ethyl-2,2,4-trimethyl hexamethylene dicarbamate
GDMA: 2-hydroxy-1,3-dimethacryloxy propane
TEGDMA: triethylene glycol dimethacrylate
bis-MEPP: 2,2-bis[4-{methacryloxyethoxy}phenyl]propane
bis-GMA: 2,2-bis[4-{3-methacryloyloxy-2-hydroxypropyl}phenyl]propane
Component (b)
CEBA: 1-cyclohexyl-5-ethyl barbiturate
BBA: 5-butyl barbiturate
Component (c)
EDTA.2Na: ethylenediamine-N,N,N',N'-tetraacetic acid-.disodium
DTPA: diethylene triamine-N,N,N',N'',N''-pentaacetic acid
CyDTA: trans-1,2-diaminocyclohexane-N,N,N',N'-tetraacetic acid
Component (d)
BPMH: 3,5,5-trimethyl hexanoate-tertiary butyl-peroxy ester
CHP: cumene hydroperoxide
Component (g)
LMAC: dilauryl dimethyl ammonium chloride
BLMAC: benzyl lauryl dimethyl ammonium chloride
LMAC: lauryl trimethyl ammonium chloride
Component (h)
CAA: acetyl acetone copper
CG: gluconate copper
CA: acetate copper
Others
DBS: dibutyl sebacate (plasticizer)
BHT: dibutyl hydroxyl toluene (polymerization inhibitor)
MEHQ: p-methoxyphenol (polymerization inhibitor)

TABLE 1A

| | | | Example 1 | Example 2 | Example 3 | Example 4 | Example 5 |
|---|---|---|---|---|---|---|---|
| First paste | Component (a) | UDMA | 59.2% | 41.4% | 31.0% | | 41.3% |
| | | GDMA | 14.8% | | | | 27.5% |
| | | TEGDMA | | 27.6% | | | |
| | | bis-MEPP | | | 46.6% | 73.7% | |
| | Component (b) | CEBA | 0.37% | 0.35% | 0.62% | 0.74% | 0.069% |
| | | BBA | | | | | |
| | Component (c) | EDTA•2Na | 0.052% | 0.056% | 0.043% | 0.044% | 0.053% |
| | | DTPA | | | | | |
| | | CyDTA | | | | | |
| | Component (d) | BPMH | 0.37% | 0.35% | 0.39% | 0.37% | 0.34% |
| | | CHP | | | | | |
| | Component (e) | fumed silica | 24.6% | 29.6% | 20.8% | 24.6% | 29.5% |
| | Component (i) | Water | 0.468% | 0.504% | 0.387% | 0.396% | 0.477% |
| | others | DBS (plasticizer) | | | | | |
| | | BHT (polymerization inhibitor) | 0.14% | 0.14% | 0.16% | 0.15% | 0.14% |
| Second paste | Component (a) | UDMA | 41.2% | 46.8% | 34.5% | 22.5% | 23.0% |
| | | GDMA | | | | | 25.5% |
| | | TEGDMA | 11.0% | 5.5% | 15.9% | 25.0% | |
| | | bis-MEPP | | | | | |
| | | bis-GMA | 2.7% | 2.72% | 2.73% | 2.34% | 2.54% |
| | Component (g) | DDDMAC | 0.08% | 0.06% | 0.05% | 0.05% | 0.05% |
| | | BDDMAC | | | | | |
| | | DTMAC | | | | | |
| | Component (h) | CAA | 0.01% | 0.01% | 0.01% | 0.01% | 0.01% |
| | | CG | | | | | |
| | | CA | | | | | |

TABLE 1A-continued

|  |  |  | Example 1 | Example 2 | Example 3 | Example 4 | Example 5 |
|---|---|---|---|---|---|---|---|
|  | Component (e) | fumed silica | 5.0% | 4.8% | 7.0% | 10.0% | 9.0% |
|  |  | silane-treated silica filler | 39.9% | 40.0% | 39.7% | 40.0% | 39.8% |
|  | others | MEHQ (polymerization inhibitor) | 0.11% | 0.11% | 0.11% | 0.10% | 0.10% |
| Confirmation of storage stability | | Curing time before storage (s) | 90 | 110 | 115 | 80 | 95 |
| | | Heat generation peak temperature before storage (° C.) | 44 | 43 | 41 | 45 | 43 |
| | | Curing time after 6 weeks at 60° C. (s) | 135 | 140 | 150 | 125 | 125 |
| | | Heat generation peak temperature after 6 weeks at 60° C. (° C.) | 37 | 39 | 37 | 40 | 37 |

TABLE 1B

|  |  |  | Example 6 | Example 7 | Example 8 | Example 9 | Example 10 |
|---|---|---|---|---|---|---|---|
| First paste | Component (a) | UDMA | 61.5% | 80.1% | 42.1% | 29.4% | 31.3% |
| | | GDMA | | | | | |
| | | TEGDMA | 26.4% | 8.9% | 42.1% | 29.4% | 31.3% |
| | | bis-MEPP | | | | | |
| | Component (b) | CEBA | 0.88% | 0.44% | 0.84% | 0.58% | 0.62% |
| | | BBA | | | | | |
| | Component (c) | EDTA·2Na | 0.050% | 0.049% | 0.049% | | |
| | | DTPA | | | | 0.4% | 0.28% |
| | | CyDTA | | | | | |
| | Component (d) | BPMH | 0.44% | 0.89% | 0.42% | 0.30% | 0.38% |
| | | CHP | 0.10% | 0.10% | 0.18% | | |
| | Component (e) | fumed silica | 10.0% | 8.9% | 13.7% | 39.8% | 36.0% |
| | Component (i) | Water | 0.450% | 0.441% | 0.441% | | |
| | others | DBS (plasticizer) | | | | | |
| | | BHT (polymerization inhibitor) | 0.18% | 0.18% | 0.17% | 0.12% | 0.12% |
| Second paste | Component (a) | UDMA | 23.0% | 24.3% | 24.3% | 61.1% | 60.0% |
| | | GDMA | 25.5% | | | 2.4% | |
| | | TEGDMA | | | | 16.2% | 19.5% |
| | | bis-MEPP | | 27.0% | 27.0% | | |
| | | bis-GMA | 2.54% | 2.6% | 2.6% | 4.0% | 3.83% |
| | Component (g) | DDDMAC | 0.05% | 0.08% | 0.08% | 0.12% | 0.17% |
| | | BDDMAC | | | | | |
| | | DTMAC | | | | | |
| | Component (h) | CAA | 0.01% | 0.01% | 0.01% | | |
| | | CG | | | | 0.02% | |
| | | CA | | | | | 0.02% |
| | Component (e) | fumed silica | 9.0% | 5.9% | 5.9% | 16.0% | 16.3% |
| | | silane-treated silica filler | 39.8% | 40.0% | 40.0% | | |
| | others | MEHQ (polymerization inhibitor) | 0.10% | 0.11% | 0.11% | 0.16% | 0.18% |
| Confirmation of storage stability | | Curing time before storage (s) | 100 | 110 | 100 | 130 | 65 |
| | | Heat generation peak temperature before storage (° C.) | 50 | 38 | 50 | 34 | 43 |

TABLE 1B-continued

|  |  | Example 6 | Example 7 | Example 8 | Example 9 | Example 10 |
|---|---|---|---|---|---|---|
|  | Curing time after 6 weeks at 60° C. (s) | 115 | 120 | 90 | 100 | 60 |
|  | Heat generation peak temperature after 6 weeks at 60° C. (° C.) | 50 | 39 | 51 | 39 | 54 |

TABLE 1C

|  |  |  | Example 11 | Example 12 | Example 13 |
|---|---|---|---|---|---|
| First paste | Component (a) | UDMA | 55.1% | 55.4% | 55.8% |
|  |  | GDMA |  |  |  |
|  |  | TEGDMA | 13.9% | 13.6% | 15.3% |
|  |  | bis-MEPP |  |  |  |
|  | Component (b) | CEBA | 0.83% | 0.86% |  |
|  |  | BBA |  |  | 0.39% |
|  | Component (c) | EDTA·2Na | 0.0001% |  | 0.10% |
|  |  | DTPA |  |  |  |
|  |  | CyDTA |  | 0.001% |  |
|  | Component (d) | BPMH | 0.33% | 0.30% | 0.36% |
|  |  | CHP |  |  |  |
|  | Component (e) | fumed silica | 29.7% | 29.7% | 27.0% |
|  | Component (i) | Water |  |  | 0.90% |
|  | others | DBS (plasticizer) |  |  |  |
|  |  | BHT (polymerization inhibitor) | 0.14% | 0.14% | 0.15% |
| Second paste | Component (a) | UDMA | 64.2% | 63.2% | 42.0% |
|  |  | GDMA |  |  |  |
|  |  | TEGDMA | 17.1% | 17.1% | 10.4% |
|  |  | bis-MEPP |  |  |  |
|  |  | bis-GMA | 4.13% | 5.1% | 2.4% |
|  | Component (g) | DDDMAC |  |  | 0.08% |
|  |  | BDDMAC | 0.09% |  |  |
|  |  | DTMAC |  | 0.12% |  |
|  | Component (h) | CAA | 0.01% | 0.01% | 0.01% |
|  |  | CG |  |  |  |
|  |  | CA |  |  |  |
|  | Component (e) | fumed silica | 14.3% | 14.3% | 5.0% |
|  |  | silane-treated silica filler |  |  | 40.0% |
|  | others | MEHQ (polymerization inhibitor) | 0.17% | 0.17% | 0.11% |
| Confirmation of storage stability | Curing time before storage (s) |  | 140 | 140 | 135 |
|  | Heat generation peak temperature before storage (° C.) |  | 38 | 36 | 34 |
|  | Curing time after 6 weeks at 60° C. (s) |  | 105 | 110 | 135 |
|  | Heat generation peak temperature after 6 weeks at 60° C. (° C.) |  | 38 | 36 | 29 |

Meanwhile, in TABLE 1A, TABLE 1B, TABLE 1C, in Examples 1 to 8 and 13, the first paste is prepared by obtaining 10% EDTA.2Na aqueous solution from EDTA.2Na in the component (c) with water in component (1).

TABLE 2

|  |  |  | Comp. ex. 1 | Comp. ex. 2 | Comp. ex. 3 | Comp. ex. 4 | Comp. ex. 5 | Comp. ex. 6 |
|---|---|---|---|---|---|---|---|---|
| First paste | Component (a) | UDMA | 14.8% | 52.6% | 56.9% | 31.6% | 56.8% | 41.5% |
|  |  | GDMA |  |  |  |  |  |  |
|  |  | TEGDMA |  |  | 14.3% |  | 14.2% |  |
|  |  | bis-MEPP | 59.2% | 35.1% |  | 47.4% |  | 13.8% |
|  | Component (b) | CEBA | 0.75% | 0.88% | 0.70% | 0.77% | 0.87% | 0.70% |
|  | Component (c) | EDTA·2Na |  |  |  |  |  |  |
|  | Component (d) | BPMH | 0.39% | 0.44% | 0.36% | 0.38% | 0.39% | 0.36% |
|  | Component (e) | fumed silica | 24.7% | 10.8% | 27.6% | 19.7% | 27.6% | 29.7% |
|  | others | DBS (plasticizer) |  |  |  |  |  | 13.8% |
|  |  | BHT (polymerization inhibitor) | 0.16% | 0.18% | 0.14% | 0.15% | 0.14% | 0.14% |
| Second paste | Component (a) | UDMA | 41.2% |  |  |  |  |  |
|  |  | TEGDMA | 11.0% |  |  |  |  |  |
|  |  | bis-GMA | 2.7% |  |  |  |  |  |
|  | Component (g) | DDDMAC | 0.08% |  |  |  |  |  |

TABLE 2-continued

|  |  | Comp. ex. 1 | Comp. ex. 2 | Comp. ex. 3 | Comp. ex. 4 | Comp. ex. 5 | Comp. ex. 6 |
|---|---|---|---|---|---|---|---|
| Component (h) | CAA | 0.01% |  |  |  |  |  |
| Component (e) | fumed silica | 5.0% |  |  |  |  |  |
|  | silane-treated silica filler | 39.9% |  |  |  |  |  |
| others | MEHQ (polymerization inhibitor) | 0.11% |  |  |  |  |  |
| Confirmation of storage stability | Curing time before storage (s) | 120 | 120 | 85 | 100 | 80 | 80 |
|  | Heat generation peak temperature before storage (° C.) | 36 | 44 | 41 | 48 | 42 | 39 |
|  | Curing time after 6 weeks at 60° C. (s) | gelate in a day | gelate in a day | gelate in a day | gelate in 10 days | gelate in a day | 80 |
|  | Heat generation peak temperature after 6 weeks at 60° C. (° C.) |  |  |  |  |  | 41 |

As is apparent from the examples, it is found that because the polymerizeble composition in two pastes form according to the embodiment of the present invention includes the amino carboxylic acid-based chelating agent of the component (c), variations in the curing time and heat generation peak temperature are small between before and after the storage.

In contrast, the composition of the comparative example, which does not include the amino carboxylic acid-based chelating agent of the component (c), gelates in a day. It is found that the storage stability is poor. Moreover, the comparative example 6 including the plasticizer of the related art has high stability, but has the problem pointed out in the related art.

That is, it is confirmed that the polymerizable composition in two pastes formed in accordance with the embodiment of the present invention is a polymerizable composition having superior characteristics with excellent storage stability while using a peroxy compound and not including plasticizer, which may be eluted in an oral cavity.

[Additional Statement]
<Polymerizable Composition in Two Pastes Form>

The embodiments of the present invention relate to a polymerizable composition used in a dental treatment, in more detail, a polymerizable composition in two pastes form which has excellent stability while including a peroxy compound and a barbiturate compound.

Then, an object of the embodiment of the present invention is to provide a new polymerizable composition, which includes a paste where a peroxy compound and a barbiturate compound are included in the same paste, and in which storage stability is enhanced without using plasticizer which may be eluted in an oral cavity.

The inventors of the present invention, in order to solve the problem, as a result of intensive research on a means for stabilizing a paste, in which a barbiturate compound and a peroxy compound are included in a (meth) acrylate compound, found that it is possible to enhance only storage stability of the paste without decreasing other features, in a case of using a specific material having a chelating effect, focusing on properties that the barbituric acid reacts sharply with metallic ions to generate a radical and that it is difficult to eliminate completely metallic ions due to incorporation during manufacturing process or from a raw material, and completes the embodiment of the present invention.

That is, the embodiment of the present invention is a polymerizable composition in two-paste form including a first paste, which includes a (meth) acrylate compound, a barbiturate compound, an amino carboxylic acid-based chelating agent, a peroxy compound and a filler, but does not include a plasticizer; and a second paste, which includes a (meth) acrylate compound, an organic halogen compound, an organic metallic compound and a filler, but does not include a plasticizer.

A first exemplary embodiment is a polymerizable composition in two-paste form including a first paste, which includes
(a) a (meth) acrylate compound,
(b) a barbiturate compound,
(c) an amino carboxylic acid-based chelating agent,
(d) a peroxy compound, and
(e) a filler,
but does not include a plasticizer; and a second paste, which includes
(a) a (meth) acrylate compound,
(g) an organic halogen compound,
(h) an organic metallic compound, and
(e) a filler,
but does not include a plasticizer.

A second exemplary embodiment is the polymerizable composition in two-paste form as described in the first exemplary embodiment including the first paste, which includes
(a) the (meth) acrylate compound in an amount of 50 to 95 wt %,
(b) the barbiturate compound in an amount of 0.1 to 2 wt %,
(c) the amino carboxylic acid-based chelating agent in an amount of 0.00001 to 2 wt %,
(d) the peroxy compound in an amount of 0.05 to 2 wt %, and
(e) the filler in an amount of 3 to 45 wt %,
but does not include the plasticizer; and the second paste, which includes
(a) the (meth) acrylate compound in an amount of 45 to 95 wt %, (g) the organic halogen compound in an amount of 0.001 to 2 wt %,
(h) the organic metallic compound in an amount of 0.001 to 0.2 wt %, and
(e) the filler in an amount of 3 to 50 wt %,
but does not include the plasticizer.

A third exemplary embodiment is the polymerizable composition in two-paste form as described in the first exemplary embodiment further including
(i) water
in the first paste.

A fourth exemplary embodiment is the polymerizable composition in two-paste form as described in the third exemplary embodiment including the first paste, which includes
(a) the (meth) acrylate compound in an amount of 50 to 95 wt %,
(b) the barbiturate compound in an amount of 0.1 to 2 wt %,
(c) the amino carboxylic acid-based chelating agent in an amount of 0.00001 to 2 wt %,
(d) the peroxy compound in an amount of 0.05 to 2 wt %,
(e) the filler in an amount of 3 to 45 wt %, and
(i) the water in an amount of 0.05 to 5 wt %,
but does not include the plasticizer; and the second paste, which includes
(a) the (meth) acrylate compound in an amount of 45 to 95 wt %,
(g) the organic halogen compound in an amount of 0.001 to 2 wt %
(h) the organic metallic compound in an amount of 0.001 to 0.2 wt %, and
(e) the filler in an amount of 3 to 50 wt %,
but does not include the plasticizer.

The embodiment of the present invention is a polymerizable composition in two-paste form having superior characteristics, with excellent storage stability while using a peroxy compound and a barbiturate compound, but not including a plasticizer which may be eluted in an oral cavity.

Although the exemplary embodiments and specific examples of the present invention are described with reference to the attached drawings, the present invention is not limited to any of the embodiments and specific examples, but various variations, modifications or combinations may be made without departing from the scope of the present invention.

The present application is based on Japanese priority application No. 2013-190281 filed on Sep. 13, 2013, with the Japanese Patent Office, the entire contents of which are hereby incorporated by reference.

What is claimed is:

1. A polymerizable composition comprising:
at least one of an acrylate compound and a methacrylate compound;
a barbiturate compound;
an amino carboxylic acid-based chelating agent;
a peroxy compound selected from the group consisting of a carboxylic acid peroxy ester or a hydroperoxide; and
a filler.

2. The polymerizable composition according to claim 1, wherein content rates of at least one of the acrylate compound and the methacrylate compound, the barbiturate compound, the amino carboxylic acid-based chelating agent, the peroxy compound and the filler in the polymerizable composition are 50 wt % to 95 wt %, 0.1 wt % to 2 wt %, 0.00001 wt % to 2 wt %, 0.05 wt % to 2 wt %, and 3 wt % to 45 wt %, respectively, and
wherein a sum of the content rates of at least one of the acrylate compound and the methacrylate compound, the barbiturate compound, the amino carboxylic acid-based chelating agent, the peroxy compound and the filler in the polymerizable composition is less than or equal to 100 wt %.

3. The polymerizable composition according to claim 1 further including water.

4. The polymerizable composition according to claim 1 further including water,
wherein content rates of at least one of the acrylate compound and the methacrylate compound, the barbiturate compound, the amino carboxylic acid-based chelating agent, the peroxy compound, the filler and water in the polymerizable composition are 50 wt % to 95 wt %, 0.1 wt % to 2 wt %, 0.00001 wt % to 2 wt %, 0.05 wt % to 2 wt %, 3 wt % to 45 wt % and 0.05 wt % to 5 wt %, respectively, and
wherein a sum of the content rates of at least one of the acrylate compound and the methacrylate compound, the barbiturate compound, the amino carboxylic acid-based chelating agent, the peroxy compound, the filler and water in the polymerizable composition is less than or equal to 100 wt %.

5. A kit for polymerizable composition comprising a first polymerizable composition and a second polymerizable composition,
wherein the first polymerizable composition includes at least one of a first acrylate compound and a first methacrylate compound, a barbiturate compound, an amino carboxylic acid-based chelating agent, a peroxy compound and a first filler,
wherein the second polymerizable composition includes at least one of a second acrylate compound and a second methacrylate compound, an organic halogen compound, an organic metallic compound and a second filler, and
wherein the peroxy compound selected from the group consisting of a carboxylic acid peroxy ester or a hydroperoxide.

6. The kit for polymerizable composition according to claim 5,
wherein content rates of at least one of the first acrylate compound and the first methacrylate compound, the barbiturate compound, the amino carboxylic acid-based chelating agent, the peroxy compound and the first filler in the first polymerizable composition are 50 wt % to 95 wt %, 0.1 wt % to 2 wt %, 0.00001 wt % to 2 wt %, 0.05 wt %, to 2 wt % and 3 wt % to 45 wt %, respectively, and
wherein a sum of the content rates of at least one of the first acrylate compound and the first methacrylate compound, the barbiturate compound, the amino carboxylic acid-based chelating agent, the peroxy compound and the first filler in the first polymerizable composition is less than or equal to 100 wt %.

7. The kit for polymerizable composition according to claim 5,
wherein the first polymerizable composition further includes water.

8. The kit for polymerizable composition according to claim 5,
wherein the first polymerizable composition further includes water,
wherein content rates of at least one of the first acrylate compound and the first methacrylate compound, the barbiturate compound, the amino carboxylic acid-based chelating agent, the peroxy compound, the first filler and water in the first polymerizable composition are 50 wt % to 95 wt %, 0.1 wt % to 2 wt %, 0.00001 wt % to 2 wt %, 0.05 wt % to 2 wt %, 3 wt % to 45 wt % and 0.05 wt % to 5 wt %, respectively, and wherein a sum of the content rates of at least one of the first acrylate compound and the first methacrylate compound, the barbiturate compound, the amino carboxylic acid-based chelating agent, the peroxy compound, the first filler and water in the first polymerizable composition is less than or equal to 100 wt %.

9. The kit for polymerizable composition according to claim 5, wherein contents rates of at least one of the second acrylate compound and the second methacrylate compound, the organic halogen compound, the organic metallic compound and the second filler in the second polymerizable composition are 45 wt % to 95 wt %, 0.001 wt % to 2 wt %, 0.001 wt % to 0.2 wt % and 3 wt % to 50 wt %, respectively, and wherein a sum of the content rates of at least one of the second acrylate compound and the second methacrylate compound, the organic halogen compound, the organic metallic compound and the second filler in the second polymerizable composition is less than or equal to 100 wt %.

10. The polymerizable composition according to claim 1, wherein the peroxy compound is selected from the group consisting of carbonate-diisopropyl-peroxy diester, neodecanoate-tertiary butyl-peroxy ester, neodecanoate-tertiary amyl-peroxy ester, maleate-tertiary butyl-mono peroxy ester, benzoate-tertiary butyl-peroxy ester, 2-ethyl hexanoate-tertiary butyl-peroxy ester, 2-ethyl hexanoate-tertiary amyl-peroxy ester, carbonate-mono isopropyl ester-mono tertiary butyl-peroxy ester, carbonate-dicyclohexyl-peroxy ester, carbonate-dimyristyl-peroxy ester, carbonate-dicetyl-peroxy ester, carbonate-di (2-ethyl hexyl)-peroxy ester, carbonate-tertiary butyl-peroxy-(2-ethyl hexyl) ester, 3,5,5-trimethyl hexanoate-tertiary butyl-peroxy ester, benzoate-tertiary amyl-peroxy ester, acetate-tertiary butyl-peroxy ester, carbonate-di (4-tertiary butyl-cyclohexyl)-peroxy ester, neodecanoate-cumene-peroxy ester, pivalate-tertiary amyl-peroxy ester, pivalate-tertiary butyl-peroxy ester, cumene hydroperoxide, 1,1,3,3-tetramethyl butyl hydroperoxide, diisopropyl benzene hydroperoxide, tertiary butyl hydroperoxide, and para-menthane hydroperoxide.

11. The polymerizable composition according to claim 1, wherein the peroxy compound is selected from the group consisting of carbonate-diisopropyl-peroxy diester, neodecanoate-tertiary butyl-peroxy ester, neodecanoate-tertiary amyl-peroxy ester, maleate-tertiary butyl-mono peroxy ester, 2-ethyl hexanoate-tertiary amyl-peroxy ester, carbonate-mono isopropyl ester-mono tertiary butyl-peroxy ester, carbonate-dicyclohexyl-peroxy ester, carbonate-dimyristyl-peroxy ester, carbonate-dicetyl-peroxy ester, carbonate-di (2-ethyl hexyl)-peroxy ester, carbonate-tertiary butyl-peroxy-(2-ethyl hexyl) ester, benzoate-tertiary amyl-peroxy ester, acetate-tertiary butyl-peroxy ester, neodecanoate-cumene-peroxy ester, pivalate-tertiary amyl-peroxy ester, pivalate-tertiary butyl-peroxy ester, 1,1,3,3-tetramethyl butyl hydroperoxide, diisopropyl benzene hydroperoxide, and para-menthane hydroperoxide.

12. The kit according to claim 5, wherein the peroxy compound is selected from the group consisting of carbonate-diisopropyl-peroxy diester, neodecanoate-tertiary butyl-peroxy ester, neodecanoate-tertiary amyl-peroxy ester, maleate-tertiary butyl-mono peroxy ester, benzoate-tertiary butyl-peroxy ester, 2-ethyl hexanoate-tertiary butyl-peroxy ester, 2-ethyl hexanoate-tertiary amyl-peroxy ester, carbonate-mono isopropyl ester-mono tertiary butyl-peroxy ester, carbonate-dicyclohexyl-peroxy ester, carbonate-dimyristyl-peroxy ester, carbonate-dicetyl-peroxy ester, carbonate-di (2-ethyl hexyl)-peroxy ester, carbonate-tertiary butyl-peroxy-(2-ethyl hexyl) ester, 3,5,5-trimethyl hexanoate-tertiary butyl-peroxy ester, benzoate-tertiary amyl-peroxy ester, acetate-tertiary butyl-peroxy ester, carbonate-di (4-tertiary butyl-cyclohexyl)-peroxy ester, neodecanoate-cumene-peroxy ester, pivalate-tertiary amyl-peroxy ester, pivalate-tertiary butyl-peroxy ester, cumene hydroperoxide, 1,1,3,3-tetramethyl butyl hydroperoxide, diisopropyl benzene hydroperoxide, tertiary butyl hydroperoxide, and para-menthane hydroperoxide.

13. The kit according to claim 5, wherein the peroxy compound is selected from the group consisting of carbonate-diisopropyl-peroxy diester, neodecanoate-tertiary butyl-peroxy ester, neodecanoate-tertiary amyl-peroxy ester, maleate-tertiary butyl-mono peroxy ester, 2-ethyl hexanoate-tertiary amyl-peroxy ester, carbonate-mono isopropyl ester-mono tertiary butyl-peroxy ester, carbonate-dicyclohexyl-peroxy ester, carbonate-dimyristyl-peroxy ester, carbonate-dicetyl-peroxy ester, carbonate-di (2-ethyl hexyl)-peroxy ester, carbonate-tertiary butyl-peroxy-(2-ethyl hexyl) ester, benzoate-tertiary amyl-peroxy ester, acetate-tertiary butyl-peroxy ester, neodecanoate-cumene-peroxy ester, pivalate-tertiary amyl-peroxy ester, pivalate-tertiary butyl-peroxy ester, 1,1,3,3-tetramethyl butyl hydroperoxide, diisopropyl benzene hydroperoxide, and para-menthane hydroperoxide.

* * * * *